US006569620B1

(12) United States Patent
Gold et al.

(10) Patent No.: US 6,569,620 B1
(45) Date of Patent: May 27, 2003

(54) METHOD FOR THE AUTOMATED GENERATION OF NUCLEIC ACID LIGANDS

(75) Inventors: Larry Gold, Boulder, CO (US); Dominic A. Zichi, Boulder, CO (US); Robert D. Jenison, Boulder, CO (US); Daniel J. Schneider, Broomfield, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 09/232,946

(22) Filed: Jan. 19, 1999

(51) Int. Cl.[7] ............................ C12Q 1/68; C12P 19/34; C12M 1/36; G01N 15/06; C07H 21/04
(52) U.S. Cl. ..................... 435/6; 435/91.2; 435/287.2; 435/288.3; 435/288.7; 435/288.4; 422/68.1; 422/63; 536/23.1
(58) Field of Search ...................... 435/6, 91.2, 287.2, 435/288.3, 288.4, 288.7; 422/63, 68.1; 536/23.1

(56) References Cited

U.S. PATENT DOCUMENTS

| 4,683,195 A | | 7/1987 | Mullis et al. | |
| 5,443,791 A | * | 8/1995 | Cathcart et al. | 422/65 |
| 5,475,096 A | * | 12/1995 | Gold et al. | 536/23.1 |
| 5,567,588 A | | 10/1996 | Gold et al. | 435/6 |
| 5,580,737 A | | 12/1996 | Polisky et al. | 435/6 |
| 5,620,850 A | | 4/1997 | Bamdad et al. | |
| 5,723,323 A | | 3/1998 | Kauffman et al. | |
| 5,861,254 A | | 1/1999 | Schneider et al. | 435/6 |
| 5,866,336 A | * | 2/1999 | Nazarenko et al. | 435/6 |
| 5,985,548 A | * | 11/1999 | Collier et al. | 435/6 |
| 6,235,471 B1 | * | 5/2001 | Knapp et al. | 435/6 |

FOREIGN PATENT DOCUMENTS

| GB | 2 183 661 A | 6/1987 |
| WO | WO 89/06694 | 7/1989 |
| WO | WO 91/19813 | 12/1991 |
| WO | WO 92/06380 | 4/1992 |
| WO | WO 92/14843 | 9/1992 |
| WO | WO 93/05182 | 3/1993 |

OTHER PUBLICATIONS

Cox et al. "Automate RNA Selection" Biotechnol. Prog., 1998, 14:845–850.*
Levisohn & Spiegelman (1968) Proc. Natl. Acad. Sci. USA 60:866.
Oliphant et al. (1989) Mol. Cell. Biol.9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Szostak (1988) "Structure and Activity of Ribozymes," in *Redesigning the Molecules of Life*, (S.A. Benner ed.) Springer–Verlag Berline Heidelberg, pp. 87–113.

(List continued on next page.)

Primary Examiner—Stephanie W. Zitomer
Assistant Examiner—B J Forman
(74) Attorney, Agent, or Firm—Swanson & Bratschun, LLC

(57) ABSTRACT

The present invention includes a method and device for performing automated SELEX. The steps of the SELEX process are performed at one or more work stations on a work surface by a cartesian robotic manipulator controlled by a computer.

10 Claims, 7 Drawing Sheets

OTHER PUBLICATIONS

Thiesen & Bach (1990) Nucleic Acids Research 18:3203.
Cheskis et al. (1996) Biochemistry 35:3309.
Cox et al. (1998) Biotechnol. Prog. 14:845–850.
Ellington & Szostak (1990) Abstracts of papers presented at the 1990 meeting on RNA Processing, Cold Spring Harbor Laboratory, Cold Spring Harbor, NY, p. 84.
Fisher et al (1994) Protein Science 3:257.
Joyce (1989) Gene 82:83.
Joyce & Inoue (1989) Nucleic Acids Research 17:711.
Karlsson (1994) Analytical Biochemistry 221:142.
Karlsson et al. (1991) J. of Immunological Methods 145:229.
Kinzler & Voglestein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Mitsuhashi, Technical Report: Part 2. Basic Requirements for Designing Optimal PCT Primers. J. of Clinical Lab. Anal. 10(5): 285–293. (1996).

* cited by examiner

SEQUENCE LISTING

<160> NUMBER OF SEQ ID NOS: 2

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic Sequence

```
-continued

<221> NAME/KEY: modified_base
<222> LOCATION: (1)..(43)
<223> OTHER INFORMATION: T at position 10 is substituted with
      DABCYL-(CH2) 6-; G at position 1 is substituted with 6-FAM

<400> SEQUENCE: 1 agcgaagct ctaatacgac tcactatagg gaggacgatg cgg                    43

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(51)
<223> OTHER INFORMATION: T at position 10 is substituted with
      DABCYL-(CH2) 6-; G at position 1 is substituted with 6-FAM

<400> SEQUENCE: 2
gagcgaagct ctaatacgac tcactatagg gagacaagaa taaacgctca a           51
```

METHOD FOR THE AUTOMATED GENERATION OF NUCLEIC ACID LIGANDS

FIELD OF THE INVENTION

This invention is directed to a method for the generation of nucleic acid ligands having specific functions against target molecules using the SELEX process. The methods described herein enable nucleic acid ligands to be generated in dramatically shorter times and with much less operator intervention than was previously possible using prior art techniques. The invention includes a device capable of generating nucleic acid ligands with little or no operator intervention.

BACKGROUND OF THE INVENTION

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Methods for Identifying Nucleic Acid Ligands", now U.S. Pat. No. 5,270,163 (see also WO 91/19813), each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands, each ligand having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The present inventors have recognized that SELEX or SELEX-like processes could be used to identify nucleic acids which can facilitate any chosen reaction in a manner similar to that in which nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (see U.S. Pat. No. 5,707,796), describes the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned (see U.S. Pat. No. 5,580,737), describes a method for identifying highly specific nucleic acid ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Known and Novel 2' Modified Nucleosides by Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S.

patent application Ser. No. 08/284,063, filed Aug. 2, 1994, entitled "Systematic Evolution of Ligands by EXponential Enrichment: Chimeric SELEX," now U.S. Pat. No. 5,637,459, and U.S. patent application Ser. No. 08/234,997, filed Apr. 28, 1994, entitled "Systematic Evolution of Ligands by EXponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes," now U.S. Pat. No. 6,011,020. Each of the above described patent applications which describe modifications of the basic SELEX procedure are specifically incorporated by reference herein in their entirety.

Given the unique ability of SELEX to provide ligands for virtually any target molecule, it would be highly desirable to have an automated, high-throughput method for generating nucleic acid ligands. The methods and instruments described herein, collectively termed automated SELEX, enable the generation of large pools of nucleic acid ligands with little or no operator intervention. In particular, the methods provided by this invention will allow high affinity nucleic acid ligands to be generated routinely in just a few days, rather than over a period of weeks or even months as was previously required. The highly parallel nature of automated SELEX process allows the simultaneous isolation of ligands against diverse targets in a single automated SELEX process experiment. Similarly, the automated SELEX process can be used to generate nucleic acid ligands against a single target using many different selection conditions in a single experiment. The present invention greatly enhances the power of the SELEX process, and will make SELEX the routine method for the isolation of ligands.

SUMMARY OF THE INVENTION

The present invention includes methods and apparatus for the automated generation of nucleic acid ligands against virtually any target molecule. This process is termed the automated SELEX process. In its most basic embodiment, the method uses a robotic manipulator to move reagents to one or more work stations on a work surface where the individual steps of the SELEX process are performed. The individual steps include: 1) contacting the candidate nucleic acid ligands with the target molecule(s) of interest immobilized on a solid support; 2) partitioning the nucleic acid ligands that have interacted in the desired way with the target molecule on the solid support away from those nucleic acids that have failed to do so; and 3) amplifying the nucleic acid ligands that have interacted with the target molecule. Steps 1–are performed for the desired number of cycles by the automated SELEX process and apparatus; the resulting nucleic acid ligands are then isolated and purified.

DETAILED DESCRIPTION OF THE FIGURES

FIG. 1 demonstrates the effect of blocking reagents on background binding of RNA to microtiter plates. The total number of RNA molecules remaining in wells of an Immulon 1 polystyrene plate, quantified with QPCR as described below are displayed for wells treated with various blocking reagents, (1) SHMCK alone, (2) SuperBlock, (3) SCHMK+Iblock, (4) SCHMK+SuperBlock, (5) SCHMK+Casein, (6) SCHMK+BSA.

FIG. 2 demonstrates the effect of buffer reagents on background binding of RNA to microtiter plates. The total number of RNA molecules remaining in unblocked wells of an Immulon 1 polystyrene plate, quantified with QPCR as described below are displayed for wells incubated and washed with solutions containing various buffer reagents, (1) SHMCK+0.1% Iblock+0.05% Tween 20 (SIT), (2) SHMCK+0.01% HSA (SA), (3) SCHMK+0.05% Tween 20 (ST), (4) SCHMK+0.01% HSA+0.05% Tween 20 (SAT), (5) SCHMK.

FIG. 3 depicts the binding and EDTA elution of aptamer 1901 from murine PS-Rg passively hydrophobically attached to an Immulon 1 polystyrene plate. Total binding of $^{32}$P labeled aptamer 1901 to wells coated with murine PS-Rg, loaded at 4.0 mg/ml, is plotted as a function of total aptamer concentration (filled circles). The amount of eluted aptamer for each of these concentrations is shown by filled triangles, and the amount of aptamer remaining in the protein coated wells after elution is shown by open squares. All samples were quantified by scintillation counting of $^{32}$P.

FIG. 4 depicts the quantification of passive adsorption of PS-Rg to Immulon 1 polystyrene plates. The amount of PS-Rg capable of binding aptamer 1901 after protein immobilization through hydrophobic interactions (filled circles) is displayed as a function of input protein concentration. The amount of active protein was obtained from the plateau values of aptamer binding curves.

FIG. 5 depicts the progress of the automated in vitro selection process. The number of RNA molecules eluted from plate wells for both manual (squares) and automated (circles) experiments are displayed for each of five rounds of SELEX performed. The amount of RNA eluted from protein coated wells is denoted by the filled markers and background binding RNA is denoted by open markers, and the amount of coated protein used in each round is denoted by x markers.

DETAILED DESCRIPTION OF THE INVENTION

Definitions

Figure 1:
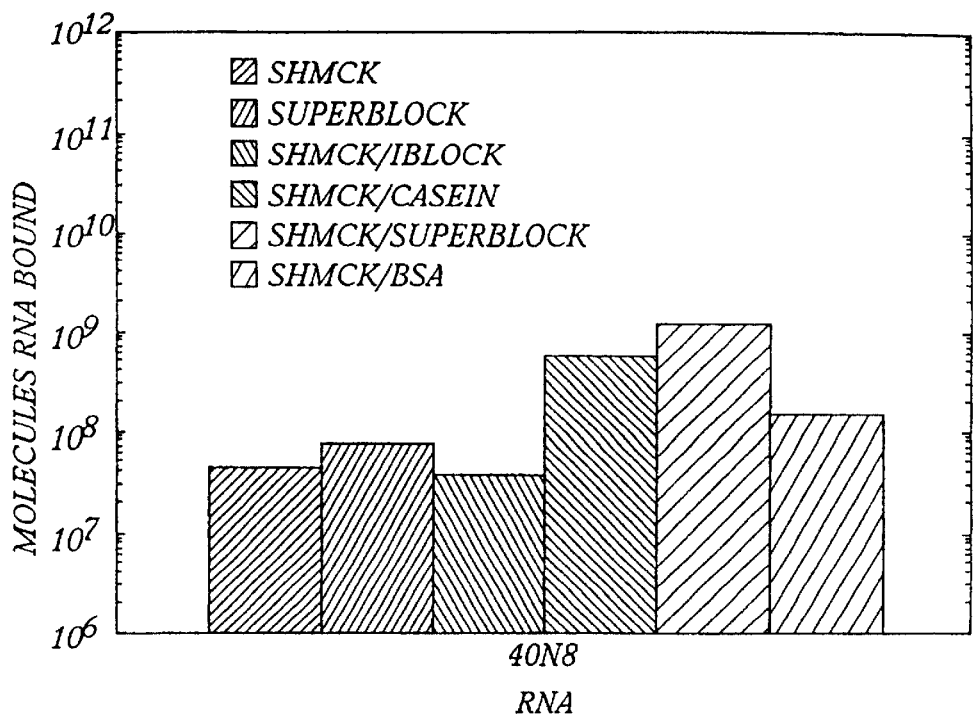

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target.

Nucleic acid ligands are also sometimes referred to in this applications as "aptamers" or "clones". A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids whereby nucleic acid ligands of the target molecule are identified.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In this invention, candidate mixture is also referred to as "40N8 RNA", or as "RNA pool". In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX methodology is described in the SELEX patent applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

As used herein, "solid support" is defined as any surface to which molecules may be attached through either covalent or non-covalent bonds. This includes, but is not limited to, membranes, plastics, paramagnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces.

"Partitioning" means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Beads upon which target molecules are conjugated can also be used to partition nucleic acid ligands in a mixture. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation, and density gradient centrifugation.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a certain amount of the nucleic acids in the candidate mixture are retained during partitioning.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX patent applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX patent applications also describe ligand solutions obtained to a number of target species, including protein targets wherein the protein is or is not a nucleic acid binding protein.

In one embodiment, the automated SELEX method uses one or more computer-controlled cartesian robotic manipulators to move solutions to and from a work station located on a work surface. The individual steps of the SELEX process are carried out at the work station. In some embodiments, each robotic manipulator is a movable arm that is capable of carrying tools in both horizontal and vertical planes. One tool contemplated is a pipetting tool. The robotic manipulator uses the pipetting tool to pick up liquid from a defined location on the work surface and then dispense the liquid at a different location. The pipetting tool can also be used to mix liquids by repeatedly picking up and ejecting the liquid i.e. "sip and spit" mixing. The robotic manipulator is also able to eject a disposable tip from the pipetting tool into a waste container, and then pick up a fresh tip from the appropriate station on the work surface.

In preferred embodiments, the pipetting tool is connected to one or more fluid reservoirs that contain some of the various buffers and reagents needed in bulk for the SELEX process. The pipetting tool is further able to eject liquid at desired locations on the work surface without the outside of the tip coming in contact with liquid already present at that location. This greatly reduces the possibility of the pipette tip becoming contaminated at each liquid dispensing step, and reduces the number of pipette tip changes that must be made during the automated SELEX process.

In some embodiments, tips that are used at certain steps of the automated SELEX process can be reused. For example, a tip can be reused if it is used in each cycle of the SELEX process to dispense the same reagent. The tip can be rinsed after each use at a rinse station, and then stored in a rack on the work surface until it is needed again. Reusing tips in this way can drastically reduce the number of tips used during the automated SELEX process.

In preferred embodiments, a vacuum aspiration system is also attached to a robotic manipulator. This system uses a fine needle connected to a vacuum source to withdraw liquid from desired locations on the work surface without immersing the needle in that liquid. The pipetting tool and the aspiration system can work simultaneously at different locations on the work surface.

In preferred embodiments, the robotic manipulator is also capable of moving objects to and from defined locations on the work surface. Such objects include lids for multi-well plates, and also the various pieces of apparatus used in the embodiments outlined below. Suitable robotic systems contemplated in the invention include the MultiPROBE™ system (Packard), the Biomek 200™ (Beckman Instruments) and the Tecan™ (Cavro).

In its most basic embodiment, the automated SELEX process method involves:

(a) contacting a candidate mixture of nucleic acid ligands in a containment vessel with a target molecule that is associated with a solid support;

(b) incubating the candidate mixture and the solid support in the containment vessel at a predetermined temperature to allow candidate nucleic acid ligands to interact with the target;

(c) partitioning the solid support with bound target and associated nucleic acid ligands away from the candidate mixture;

(d) optionally washing the solid support under predetermined conditions to remove nucleic acid that are associated non-specifically with the solid support or the containment vessel;

(e) releasing from the solid support the nucleic acid ligands that interact specifically with the target;

(f) amplifying, purifying and quantifying the released nucleic acid ligands;

(g) repeating steps (a)–(f) a predetermined number of times; and (h) isolating the resulting nucleic acid ligands.

Steps (a)–(g) are performed automatically by the computer-controlled robotic manipulator. The computer also measures and stores information about the progress of the automated SELEX process procedure, including the amount of nucleic acid ligand eluted from the target molecule prior to each amplification step. The computer also controls the various heating and cooling steps required for the automated SELEX process.

In preferred embodiments, the work surface comprises a single work station where the individual SELEX reactions take place. This station comprises heating and cooling means controlled by the computer in order to incubate the reaction mixtures at the required temperatures. One suitable heating and cooling means is a Peltier element. The work station preferably also comprises a shaking mechanism to insure that SELEX reaction components are adequately mixed. The work surface also comprises stations in which the enzymes necessary for SELEX are stored under refrigeration, stations where wash solutions and buffers are stored, stations where tools and apparatus are stored, stations where tools and apparatus may be rinsed, and stations where pipette tips and reagents are discarded. The work surface may also comprise stations for archival storage of small aliquots of the SELEX reaction mixtures. These mixtures may be automatically removed from the work station by the pipetting tool at selected times for later analysis. The work surface may also comprise reagent preparation stations where the robotic manipulator prepares batches of enzyme reagent solutions in preparation vials immediately prior to use.

In other embodiments, the work surface comprises more than one work station. In this way, it is possible to perform the individual steps of the automated SELEX process asynchronously. For example, while a first set of candidate nucleic acid ligands is being amplified on a first work station of step (f), another set from a different experiment may be contacted with the support-bound target molecule of step (b) on a different work station. Using multiple work stations minimizes the idle time of the robotic manipulator.

In still other embodiments, the individual steps of the automated SELEX process are carried out at discrete work stations rather than at a single multi-functional work station. In these embodiments, the solutions of candidate nucleic acid mixtures are transferred from one work station to another by the robotic manipulator. Separate work stations may be provided for heating and cooling the reaction mixtures.

In preferred embodiments, the individual steps of the automated SELEX process are carried out in a containment vessel that is arranged in an array format. This allows many different SELEX reactions—using different targets or different reaction conditions—to take place simultaneously on a single work station. For example, in some embodiments the individual steps may be performed in the wells of microtitre plates, such as Immulon 1 plates. In other embodiments, an array of small plastic tubes is used. Typical tube arrays comprise 96 0.5 ml round-bottomed, thin-walled polypropylene tubes laid out in a 8×12 format. Arrays can be covered during the heating and cooling steps to prevent liquid loss through evaporation, and also to prevent contamination. Any variety of lids can be placed over the arrays by the robotic manipulator during these times. Furthermore, arrays allow the use of multipipettor devices: this can greatly reduce the number of pipetting steps required. For the purposes of this specification, the term "well" will be used to refer to an individual containment vessel in any array format.

Solid supports suitable for attaching target molecules are well known in the art. Any solid support to which a target molecule can be attached, either covalently or non-covalently, is contemplated by the present invention. Covalent attachment of molecules to solid supports is well known in the art, and can be achieved using a wide variety of derivatization chemistries. Non-covalent attachment of targets can depend on hydrophobic interactions; alternatively, the solid support can be coated with streptavidin which will bind strongly to a target molecule that is conjugated to biotin.

In particularly preferred embodiments, the solid support is a paramagnetic bead. When target molecules are attached to paramagnetic beads, complexes of target molecules and nucleic acid ligands can be rapidly partitioned from the candidate mixture by the application of a magnetic field to the wells. In preferred embodiments, the magnetic field is applied by an array of electromagnets adjacent to the walls of each well; when the electromagnets are activated by the computer, paramagnetic target beads are held to the sides of the wells. The magnets can either be an integral part of the work station, or they can be attached to a cover that is lowered over the work station by the robotic manipulator. In this latter embodiment, the magnetic separator cover allows the magnets to be placed adjacent to the wells without blocking access to the wells themselves. In this way, the wells are accessible by the pipetting and aspirating units when the cover is in place. Following magnet activation, liquid can be aspirated from the wells, followed by the addition of wash solutions. When the electromagnets are deactivated, or when the cover is removed, the beads become resuspended in the solution. The magnetic separator cover can be stored on the work surface. In other embodiments, the magnets in the separator cover are permanent magnets. In this case, withdrawing the cover removes the influence of the magnets, and allows the beads to go into suspension.

The paramagnetic target beads used in the above embodiments are preferably stored on the work surface in an array format that mirrors the layout of the array format on the work station. The bead storage array is preferably cooled, and agitated to insure that the beads remain in suspension before use.

Beads can be completely removed from the wells of the work station using a second array of magnets. In preferred embodiments, this second array comprises an array of electromagnets mounted on a cover that can be placed by the robotic manipulator over the surface of the individual wells on the work station. The electromagnets on this bead removal cover are shaped so that they project into the liquid in the wells. When the electromagnets are activated, the beads are attracted to them. By then withdrawing the bead removal cover away from the wells, the beads can be efficiently removed from the work station. The beads can either be discarded, or can be deposited back in the bead storage array for use in the next cycle of automated SELEX. The bead removal cover can then be washed at a wash station on the work surface prior to the next bead removal step.

In a typical embodiment involving paramagnetic beads, the automated SELEX process begins when the pipetting tool dispenses aliquots of the beads—with their bound target—to the individual wells of a microtitre plate located on the work station. Each well already contains an aliquot of a candidate mixture of nucleic acid ligands previously dispensed by the robotic manipulator. After dispensing the beads, the robot optionally "sips and spits" the contents of each well up and down several times to facilitate thorough mixing. The microtitre plate is then incubated at a preselected temperature on the work station in order to allow nucleic acid ligands in the candidate mixture to bind to the bead-bound target molecule. Agitation of the plate insures that the beads remain in suspension.

After incubation for a suitable time, the magnetic separator cover is placed over the microtitre plate by the robotic manipulator. The beads are then held to the sides of the wells, and the aspirator tool removes the solution containing unbound candidate nucleic acids from the wells. A washing solution, such as a low salt solution, can then be dispensed into each well by the pipetting tool. The beads are released from the side of the wells by withdrawing the magnetic separator cover or deactivating the electromagnets, then resuspended in the wash solution by agitation and "sip and spit" mixing. The magnetic separator cover is placed over the plate again, and the wash solution is aspirated. This wash loop can be repeated for a pre-selected number of cycles. At the end of the wash loop, the beads are held by the magnets to the sides of the empty wells.

The beads can then be resuspended in a solution designed to elute the nucleic acid ligands from the target molecule, such as $dH_2O$. The dissociation of nucleic acid ligand from target can also be achieved by heating the beads to a high temperature on the work station.

After dissociation of the nucleic acid ligands from the bead-bound target, the pipetting tool can dispense into the wells the enzyme and buffer components necessary to perform amplification of the candidate nucleic acid ligands. After amplification, purification and quantification (see below), a predetermined amount of the amplified candidate mixture can then used in the next cycle of the automated SELEX process. At any point during the cycles, the pipetting tool can remove an aliquot of the candidate mixture and store it in an archive plate for later characterization. Furthermore, during incubation periods, the pipetting tool can prepare reaction mixtures for other steps in the SELEX process.

As described above, the preferred embodiments of the automated SELEX process method and apparatus use microtitre plates and magnetic beads to achieve selection. However, any other method for partitioning bound nucleic acid ligands from unbound is contemplated in the invention. For example, in some embodiments, the target molecule is coupled directly to the surface of the microtitre plate. Suitable methods for coupling in this manner are well known in the art.

In other embodiments, the target molecule is coupled to affinity separation columns known in the art. The robotic device would dispense the candidate mixture into such a column, and the bound nucleic acid ligands could be eluted into the wells of a microtitre plate after suitable washing steps.

In still other embodiments, the solid support used in the automated SELEX process method is a surface plasmon resonance (SPR) sensor chip. The use of SPR sensor chips in the isolation of nucleic acid ligands is described in WO 98/33941 entitled "Flow Cell SELEX", incorporated herein by reference in its entirety. In the Flow Cell SELEX method, a target molecule is coupled to the surface of a surface plasmon resonance sensor chip. The refractive index at the junction of the surface of the chip and the surrounding medium is extremely sensitive to material bound to the surface of the chip. In one embodiment of the present invention, a candidate mixture of nucleic acid ligands is passed over the chip by the robotic device, and the kinetics of the binding interaction between the chip-bound target and nucleic acid ligands is monitored by taking readings of the resonance signal from the chip. Such readings can be made using a device such as the BIACore 2000™ (BIACore, Inc.). Bound nucleic acid ligands can then be eluted from the chip; the kinetics of dissociation can be followed by measuring the resonance signal. In this way it is possible to program the computer that controls the automated SELEX process to automatically collect nucleic acid ligands which have a very fast association rate with the target of interest and a slow off rate. The collected nucleic acid ligands can then be amplified and the automated SELEX process cycle can begin again.

In still other embodiments, the solid support is a non-paramagnetic bead. Solutions can be removed from the wells containing such beads by aspirating the liquid through a hole in the well that is small enough to exclude the passage of the beads. For example, a vacuum manifold with a $0.2 \mu M$ filter could be used to partition $100 \mu M$ beads.

At the end of the automated SELEX process, the resulting nucleic acid ligands can be isolated from the automated SELEX process apparatus for sequence analysis and cloning.

Amplification of the Candidate Nucleic Acid Ligands

At the end of each binding and partitioning step in the automated SELEX process method, the candidate nucleic acid ligands must be amplified. In preferred embodiments, the amplification is achieved using the Polymerase Chain Reaction (PCR). As the candidate nucleic acid ligands in the automated SELEX process method preferably all have fixed 5' and 3' regions, primers that bind to these regions are used to facilitate PCR.

In embodiments that use target beads, the beads are removed from the wells before beginning the amplification procedure. When paramagnetic beads are used, this can be done using the magnetic removal system described above.

Candidate nucleic acid ligands can be single-stranded DNA molecules, double-stranded DNA molecules, single-stranded RNA molecules, or double-stranded RNA molecules. In order to amplify RNA nucleic acid ligands in a candidate mixture, it is necessary to first reverse transcribe the RNA to cDNA, then perform the PCR on the cDNA. This process, known as RT-PCR, can be carried out using the automated SELEX process method by dispensing the necessary enzymes, primers and buffers to the wells on the work station containing the eluted ligand. The resulting reaction mixtures are then first incubated on the work station at a temperature that promotes reverse transcription. After reverse transcription, the work station thermally-cycles the reaction mixtures to amplify the cDNA products. The amount of amplified product is then measured to give a value for the amount of candidate nucleic acid ligand eluted from the target (see below).

For RNA ligands, the amplified DNA molecules must be transcribed to regenerate the pool of candidate RNA ligands for the next cycle of automated SELEX. This can be achieved by using primers in the amplification step that contain sites that promote transcription, such as the T7 polymerase site. These primers become incorporated into the amplification product during the PCR step. Transcription from these sites can be achieved simply by dispensing the appropriate enzymes and buffer components into the amplified mixtures and then incubating at the appropriate temperature. A predetermined amount of the amplified mixture is then used in the next cycle of the automated SELEX process.

Purification of RNA Ligands from Amplification Mixtures

In some embodiments, amplified RNA ligands are purified from their DNA templates before beginning the next cycle of automated SELEX. This can be done using a second set of paramagnetic beads to which primers complementary to the 3' constant region of the RNA ligands are attached. When these primer beads are added to the transcribed amplification mixture, the newly transcribed full length RNA ligands hybridize to the bead-bound primer, whereas the amplified double-stranded DNA molecules remain in solution. The beads can be separated from the reaction mixture by applying a magnetic field to the wells and aspirating the liquid in the wells, as described above. The beads can then be washed in the appropriate buffer at a preselected temperature, and then the RNA ligands may be eluted from the beads by heating in an elution buffer (typically $dH_2O$). Finally, the beads may be removed from the wells on the work station, as described above to leave only a solution of candidate RNA ligands remaining in the wells. This point marks the completion of one cycle of the automated SELEX procedure.

The amount of primer bead added determines the amount of RNA ligand that is retained in the wells. Therefore, the amount of RNA ligand that is used in the next cycle of the automated SELEX procedure can be controlled by varying the amount of primer bead that is added to the amplification mixture. The amount of RNA ligand that is to be used can be determined through quantitation of the amount of PCR product (see below).

Calculation of the Amount of Eluted Nucleic Acid Ligand in Each Amplification Mixture In certain embodiments, it may be important to measure the amount of candidate nucleic acid ligand eluted from the target before beginning the next cycle of the automated SELEX process. Such measurements yield information about the efficiency and progress of the selection process. The measurement of eluted nucleic acid ligand—which serves as template for the amplification reaction—can be calculated based on measurements of the amount of amplification product arising out of each PCR reaction.

In preferred embodiments, the automated SELEX process method uses a novel system for the automated real-time quantitation of PCR products during amplification. This, in turn, permits the progress of the selection experiment to be monitored in real time during the automated SELEX process. In preferred embodiments, the automated SELEX process method uses a fluorophore/quencher pair primer system. This system is used to calculate automatically the amount of eluted nucleic acid ligand introduced into the reaction mixture by measuring the fluorescence emission of the amplified mixture. In one such embodiment of the invention, the PCR reaction is carried out using primers that have a short hairpin region attached to their 5' ends. The stem of the hairpin has a fluorophore attached to one side and a quencher attached on the other side opposite the fluorophore. The quencher and the fluorophore are located close enough to one another in the stem that efficient energy transfer occurs, and so very little fluorescent signal is generated upon excitation of the fluorophore. Examples of such primers are described in Example 2. During the PCR reaction, polymerase extension of the 3' end of DNA molecules that anneal to the primer disrupts the stem of the hairpin. As a result, the distance between the quencher and the fluorophore increases, and the efficiency of quenching energy transfer drops dramatically. An incorporated primer therefore has a much higher fluorescence emission signal than an unincorporated primer. By monitoring the fluorescence signal as a function of the PCR cycle number, PCR reaction kinetics can be monitored in real time. In this way, the amount of candidate nucleic acid ligand eluted from target in each reaction can be quantitated. This information in turn is used to follow the progress of the selection process.

In other embodiments, the candidate nucleic acid ligand templates are quantitated using the TaqMan™ probe PCR system available from Roche Molecular Systems. Briefly, a TaqMan™ probe is an oligonucleotide with a sequence complementary to the template being detected, a fluorophore on the 5' end, and a quencher on the 3' end. The probe is added to a standard PCR reaction and anneals to the template between the primer binding sites during the annealing phase of each PCR cycle. During the extension phase, the probe is degraded by the 5'→3' exonuclease activity of Taq Polymerase, separating the fluorophore from the quencher and generating a signal. Before PCR begins, the probe is intact and the excitation energy of the fluorophore is non-radioactively transferred to the quencher. During PCR, as template is amplified, the probe is degraded and the amount of fluorescent signal generated is directly proportional to the amount of PCR product formed.

The current invention contemplates the use of fluorometry instruments that can monitor the fluorescence emission profile of the reaction mixture(s) on the work station during thermal-cycling. Suitable instruments contemplated comprise a source for excitation of the fluorophore, such as a laser, and means for measuring the fluorescence emission from the reaction mixture, such as a Charge Coupled Device (CCD) camera. Appropriate filters are used to select the correct excitation and emission wavelengths. Especially preferred embodiments use a fluorometry instrument mounted on an optically-transparent cover that can be placed over the wells on the work station by the robotic manipulator. When placed over the wells and then covered with a light shield, this fluorometry cover can capture an image of the entire array at pre-selected intervals. The computer interprets this image to calculate values for the amount of amplified product in each well at that time. At the end of the amplification step, the robotic manipulator removes the light shield and fluorometry cover and returns them to a storage station on the work surface.

In preferred embodiments, measurements of PCR product quantity are used to determine a value for the amount of eluted nucleic acid ligand introduced as template into the amplification reaction mixture. This can be done by comparing the amount of amplified product with values stored in the computer that were previously obtained from known concentrations of template amplified under the same conditions. In other embodiments, the automated SELEX process apparatus automatically performs control PCR experiments with known quantities of template in parallel with the candidate nucleic acid amplification reactions. This allows the computer to re-calibrate the fluorescence detection means internally after each amplification step of the automated SELEX process.

The value for the amount of candidate nucleic acid ligand eluted from the target is used by the computer to make optimizing adjustments to any of the steps of the automated SELEX process method that follow. For example, the computer can change the selection conditions in order to increase or decrease the stringency of the interaction between the candidate nucleic acid ligands and the target. The computer can also calculate how much of the nucleic acid ligand mixture and/or target bead should be used in the next SELEX cycle. In embodiments using primer beads (above), the computer uses this information to determine the amount of primer bead suspension to be added to each well on the work station. Similarly, the computer can change the conditions under which the candidate nucleic acid ligands are amplified. All of this can be optimized automatically without the need for operator intervention.

FIGS. 7–10 show various views of an embodiment of an apparatus for performing automated SELEX according to the present invention.

EXAMPLES

The examples below are illustrative embodiments of the invention. They are not to be taken as limiting the scope of the invention.

Example 1

The basis of the robotic workstation is a Packard MULTIProbe 204DT™, a four probe pipetting station that utilizes disposable pipette tips to minimize nucleic acid contamination. The workspace contains a 37° C. constant temperature heat block used for equilibration of the binding reaction and in vitro transcription, a computer controlled thermal cycler for both RT and PCR reactions, a freezer unit for cold enzyme storage, various vessels for reagent storage, e.g., buffers, primers, and mineral oil, and disposable pipette tip racks. The tip racks utilize the greatest area on the work surface and vary depending on the number of samples processed in parallel. All steps for in vitro selection take place either on the heat block or in the thermal cycler, liquids are transferred primarily between these two stations, although some enzyme buffers are premixed in an adjacent reagent block prior to transfer to the plate or thermal cycler.

The entire process is controlled by a PC with software developed in-house in HAM (High level Access Method), a DOS based C programming language interpreter augmented with liquid handling functions for the Packard MULTIProbe. In addition to standard C functionality and liquid handling, such as aspirating, dispensing, and mixing fluids, HAM supports window based screen io, file handling, and RS-232 serial communications. The software automatically adjusts the process to run any number of samples between one and 96, preparing only those enzyme solutions necessary during the current run. Two way communication with the thermal cycler, established with an RS-232 connection, allows the main computer to perform lid opening/closing operations, initiate programs stored on thermal cycler, and monitor thermal cycler programs for completion. The overall software design enables complete computer control of the process, from binding reaction incubation through transcription, to occur with no user intervention.

The process begins by placing a microtiter plate coated with protein on the 37° C. block. All subsequent liquid handling up to gel purification of the enriched RNA pool is controlled by the software. During the initial two hour incubation of RNA with immobilized protein target, $dH_2O$ is periodically added to the samples (to control evaporative loss) and each solution is mixed by repeated aspiration and dispensing, so-called sip-and-spit. After the binding reaction has equilibrated, partitioning bound from free RNA is easily accomplished in this format by simply removing the RNA solution from each well; bound nucleic acid remains on the immobilized target and unbound molecules are disposed. Partitioning is followed by a series of wash steps, each wash comprised of pipetting a wash buffer solution into each well with subsequent repeated sip-and-spit mixing and finally disposal of the wash solution. The elution process begins by addition of EDTA followed by a 30 minute incubation with periodic sip-and-spit mixing. After incubation, the solution is transferred to the thermal cycler and the wells washed as described above, with the exception that each wash solution here is added to the eluted material in the cycler. The sample is then ready for enzymatic amplification.

The first step for each of the three enzyme reactions requires the preparation of a fresh enzyme solution. This is done by pipetting an aliquot of enzyme from the freezer to the appropriate buffer located in the reagent block. The viscous enzyme solution is mixed carefully and thoroughly using slow sip-and-spit mixing to avoid foaming of detergents in the enzyme solution. An aliquot of the freshly prepared RT reaction mixture is added to the dry wells of the eluted plate for a wash to remove possible eluted RNA remaining in the well. The RT reaction mixture wash is then added to the appropriate well in the thermal cycler and capped with silicone oil to prevent evaporative loss during reaction incubation at 48° C. The thermal cycler lid is closed and a program initiated for the RT reaction. The main computer monitors the reaction progress and upon detecting program completion, the lid is opened, a Taq polymerase reaction mixture is prepared and added to each completed RT reaction. This is followed by lid closure, PCR program initiation, monitoring and lid opening upon completion of PCR. An aliquot of the amplified DNA is moved from the thermal cycler to appropriate wells in the 37° C. plate for in vitro transcription of the DNA template. A freshly prepared T7 RNA polymerase solution is added to each well thoroughly mixed. A layer of silicone oil caps the reaction mixture that then incubates for 4 hours. This completes the automated process; the resulting transcribed RNA is gel purified off line and added to a microtiter plate with freshly coated protein wells for the next round of SELEX.

Typical Automated SELEX Process Run

A typical automated SELEX process run using a multi-well plate begins with loading the various reagents and materials needed to the appropriate locations on the work surface. The following steps then take place (each step performed by robot):

1) Pipette candidate nucleic acid mixture to each well of a 96 well plate on work station with one tip; tip disposed.

2) Pipette target paramagnetic beads to each well of the 96 well plate on work station; tip disposed.

3) Binding

Plate incubated at 37° C. with shaking for 30–120 minutes to allow nucleic acid ligands to interact with target on bead.

4) Bead Separation and Washing

Separate beads by placing magnetic separator cover on plate; aspirate liquid from wells; remove magnetic separator cover; dispense washing buffer to each well; incubate at 37° C. for 5 minutes with shaking.

5) Repeat step 4) for the desired number of wash cycles.

6) Elution 1

Separate beads by placing magnetic separator cover on plate and aspirate liquid from wells; remove magnetic separator cover and resuspend beads in each well in 90 $\mu$L of $dH_2O$; heat plate to 90° C. with shaking to elute nucleic acid ligands.

7) Cool plate to 48° C.

8) Prepare PCR reaction mixture in preparation vial on work surface using buffers and reverse transcriptase.

9) Pipette aliquot of PCR reaction mixture to each well on work station.

10) Reverse Transcription

Incubate plate on work station at 48° C. for 30 minutes with shaking to allow reverse transcription to take place.

11) Bead Removal 1

Place bead removal cover on plate to capture beads on magnets; move removal cover and attached beads to drop station; drop beads at drop station and wash cover at wash station.

12) Place fluorometry cover over plate on work station; place light shield over work station.

13) Amplification

Thermally cycle plate until fluorometry cover indicates that DNA saturation has occurred; calculate the amount of amplification product in each well using fluorometer readings.

14) Remove light shield and fluorometry cover; remove aliquot from each well and dispense in an archive array for storage.

15) Prepare transcription mixture in preparation vial on work surface using buffers and RNA polymerase.

16) Pipette aliquot of transcription mixture to each well on work surface.

17) Transcription

Incubate plate on work surface at 37° C. for 4 hours with shaking to allow transcription to take place.

18) Purification

Determine volume of primer paramagnetic beads needed to retain the desired amount of RNA from each well; dispense the calculated quantity of beads to each well on work surface.

19) Incubate plate on work surface at 48° C. for 5 minutes with shaking.

20) Bead Separation and Washing

Separate primer beads by placing magnetic separation cover on plate; aspirate each well; remove separation cover; pipette wash buffer to each well; incubate plate at 48° C. for 5 minutes with shaking.

21) Repeat step 20) for the desired number of wash cycles.

22) Elution 2

Separate beads by placing magnetic separation cover on plate; aspirate each well; remove separation cover; pipette 100 μL dH$_2$O to each well; incubate plate on work station at 95° C. for 3 minutes with shaking to elute RNA from primer beads.

23) Bead Removal 2

Place bead removal cover on plate to capture beads on magnets; move removal cover and attached beads to drop station; drop beads at drop station and wash cover at wash station.

24) Begin at step 2) again for the desired number of cycles.

Example 2

The following example describes the performance of automated SELEX on the recombinant murine selectin/IgG fusion protein. For a description of manual SELEX against selection targets see U.S. Pat. No. 5,780,228.

Automated Selection

Murine PS-Rg, a recombinant murine selectin/IgG fusion (purchased from D. Vestweber) was manually coated in concentrations stated in results in 75 μl SHMCK buffer (10 mM HEPES pH 7.3, 120 mM NaCl, 5 mM KCl, 1 mM MgCl$_2$, 1 mM CaCl$_2$) for two hours at room temperature (23° C.) onto a round bottom Immulon 1 polystyrene 96 well microtiter plate. Control wells were prepared by coating SHMCK alone. The plate was then washed six times with 150 μl SAT (SHMCK, 0.01% HSA (Sigma), 0.05% Tween 20 (Aldrich) and 200 pmoles of gel purified RNA pool was added in 75 μl SAT buffer. The plate was placed on a 37° C. heat block (USA Scientific) mounted on a MultiPROBE 204DT pipetting workstation (Packard) and samples were incubated uncovered at 37° C. for two hours. All subsequent steps were performed by the robotic workstation except where noted. Every twenty minutes during the incubation of the RNA with the plate 5 μl of dH$_2$O was added to compensate for evaporative loss (rate of loss measured at 14.5+0.4 μl/hour) and to mix the reactions. Plates were then washed six times with 150 μl SAT buffer.

To the dried plate 75 μl of SHKE (10 mM HEPES pH 7.3, 120 mM NaCl, 5 mM KCl, 5 mM EDTA) was added to the plate and incubated at 37° C. for 30 minutes with mixing every ten minutes. The supernatant was then removed from the plate and added to an MJ Research thermocycler mounted on the work station with remote command capabilities.

Automated Amplification

AMV reverse transcriptase(Boeringer Mannheim) stored in a pre-chilled Styrofoam cooler mounted on the work surface at below 0° C., was added to a prepared RT buffer and thoroughly mixed. 25 μl of the resulting RT Mix (50 mM Tris-HCL pH 8.3, 60 mM NaCl, 11 mM Mg(OAc)$_2$, 10 mM DTT, 1 mM dATP, 1 mM dTTP, 1 mM dGTP, 1 mM dCTP, 400 pmoles 3P8, 20 units AMV-RT/reaction) was then added to the empty incubation wells and mixed to provide a wash for the well. The RT mix was then moved into the thermocycler, added to the eluted RNA, and thoroughly mixed. To this 25 μl of silicone oil (Aldrich) was added to prevent evaporation. The thermocycler was then remotely turned on by the computer. The lid was closed and the reaction incubated at 48° C. for 30 minutes followed by 60° C. for 5 minutes. Upon completion of the RT reaction the lid was triggered to open and 10 μl of the reaction was manually removed to be measured manually by quantitative PCR (qPCR).

Taq polymerase(Perkin Elmer) stored in the Styrofoam cooler, was added to a prepared PCR buffer (Perkin Elmer Buffer 2 (50 mM KCL, 10 mM Tris-HCl pH 8.3), 7.5 mM MgCl$_2$, 400 pmoles 5P8) and thoroughly mixed. 100 μl of the Taq mix was then added to each well, the lid closed, and PCR was initiated. PCR was run under the following conditions: 93° C. for 3 minutes followed by a loop consisting of 93° C. for 1 minute, 53° C. for 1 minute, and 72° C. for 1 minute for n cycles where n was determined by the input amount of RNA to the RT reaction (see qPCR description). Upon completion of PCR the lid was opened and 50 μl was removed and added to an empty plate well on the fixed 37° C. heat block.

T7 RNA polymerase (Enzyco) stored in the Styrofoam cooler, was added to a prepared Transcription buffer (40 mM Tris-HCl pH 8, 4% (w/v) PEG-8000,12 mM MgCl$_2$, 5 mM DTT, 1 mM Spermidine, 0.002% Triton X-100, 100 units/ml pyrophosphatase (Sigma)) and thoroughly mixed. 200 μl of the Transcription buffer was then added to the PCR product well and mixed. To this reaction a 25 μl layer of silicone oil was added and the reaction was incubated for 4 hours at 37° C. The completed reaction was then removed and purified manually by PAGE.

Plate Characterization

1. Test of Various Blocking Agents

To empty Immulon 1 wells, 150 μl of various buffers were incubated for 30 minutes at room temperature including the following:

(1) SHMCK (2) SuperBlock (Pierce)

(3) SHMCK+0.1% I-Block (Tropix)

(4) SHMCK+0.1% Casein (Sigma)

(5) SHMCK+SuperBlock (1:1)

(6) SHMCK+1% BSA

The wells were then washed six times with 150 μl of SIT buffer. Then 200 pmoles of 40N8 RNA in SIT buffer were added to each well and incubated for 2 hours at 37° C. The wells were washed six times with 150 μl SIT buffer. To each well 75 μl of dH$_2$O was added and heated to 95° C. for 5 minutes to elute the RNA from the plate. To this 25 μl of an RT mix was added and incubated as described. The eluant was then measured offline for amount of RNA present by qPCR. The results of this experiment are shown in FIG. 1.

2. Role of Buffer Components in Background on Unblocked Immulon 1 Plates

To empty Immulon 1 wells, 200 pmoles of 40N8 was added in 100 μl of the following buffers and incubated at 37° C. for 2 hours:

(1) SIT (SHMCK, 0.1% I-Block, 0.05% Tween 20)

(2) SHMCK (3) SA (SHMCK, 0.01% HSA)

(4) ST (SHMCK, 0.05% Tween 20)

(5) SAT (SHMCK, 0.01% HSA, 0.05% Tween 20)

Figure 2:
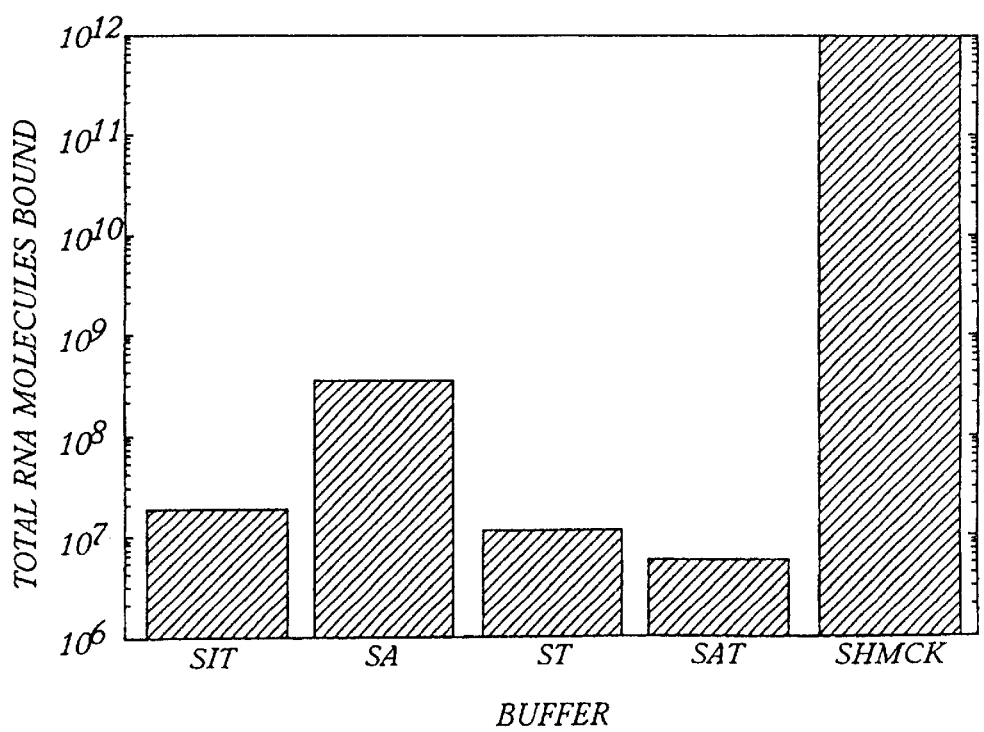

The wells were subsequently washed six times with 150 μl of the appropriate buffer and eluted with SHKE as described. The eluant was then measured for the amount of RNA present by RT as described followed by qPCR. The results of this experiment are shown in FIG. 2.

EDTA Elution Study with Murine PS-Rg

Figure 3:
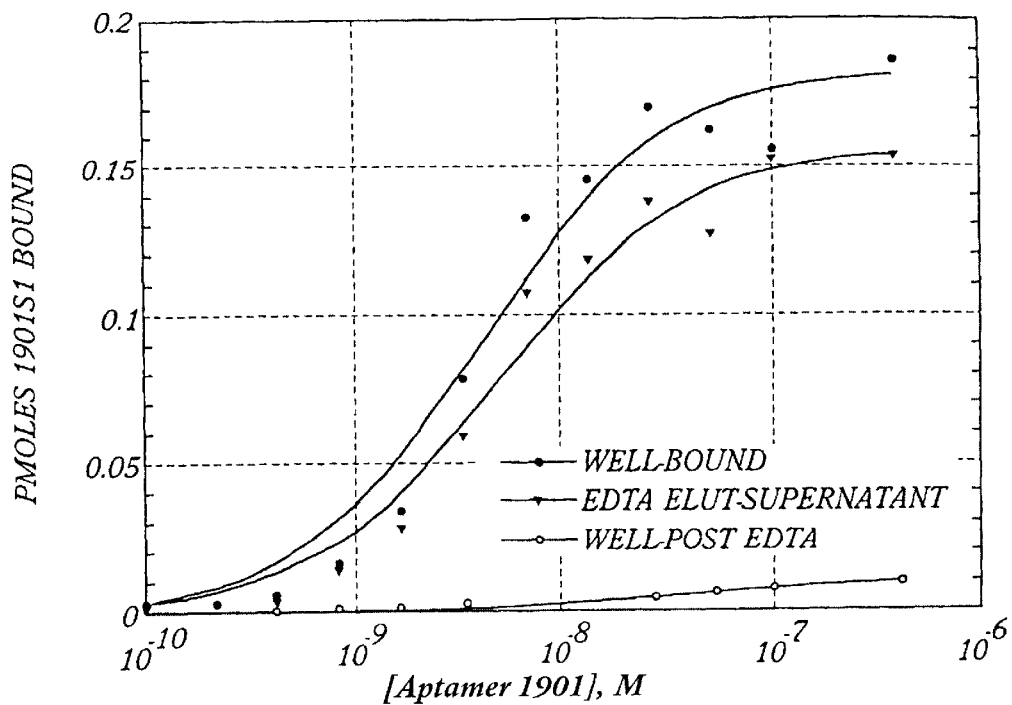

4 μg/ml murine PS-Rg was coated onto empty wells in 75 μl SHMCK for 2 hours at room temperature and washed as described. Then a titration of 3 fmoles to 20 pmoles of RNA clone #1901, isolated from a previous manual SELEX experiment, was coated on two sets of control and PS-Rg wells for 2 hours at 37° C. and washed as described. One set of control and PS-Rg wells were then removed and monitored for $^{32}$P-RNA bound by scintillation counting. 50 µl of SHKE was then added to the other set of dry wells and incubated with mixing at 37° C. for 30 minutes. The buffer was then removed and $^{32}$P-labeled RNA was measured by scintillation counting. The results of this experiment are shown in FIG. 3.

SELEX Progress

Figure 4:
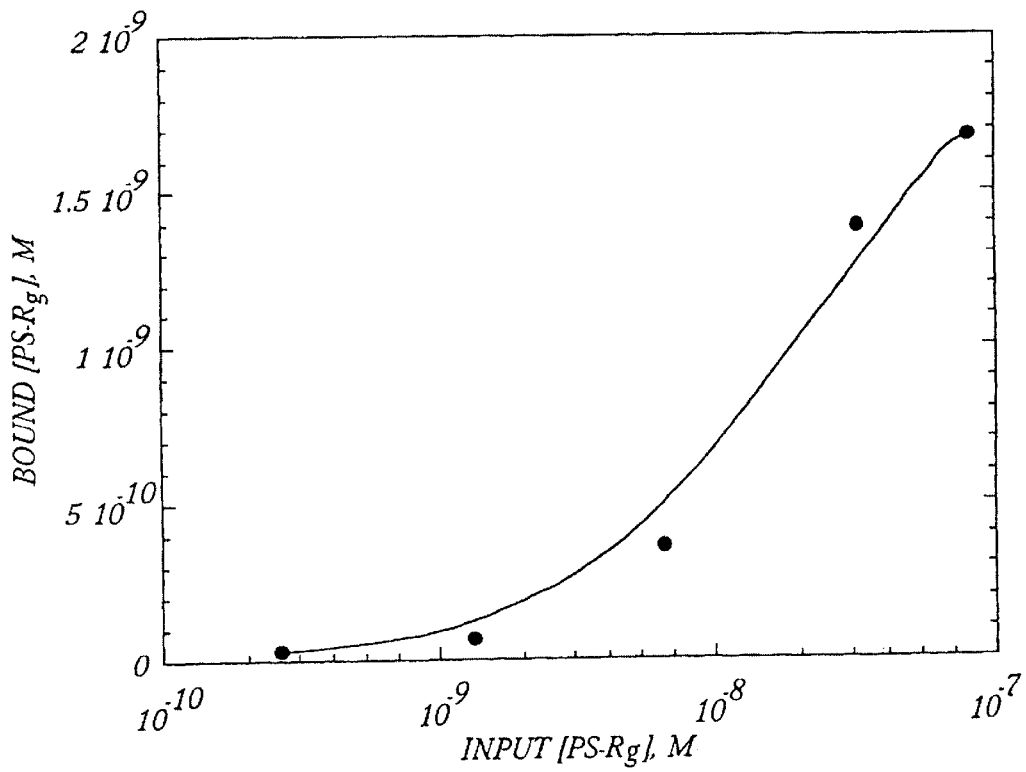
Figure 5:
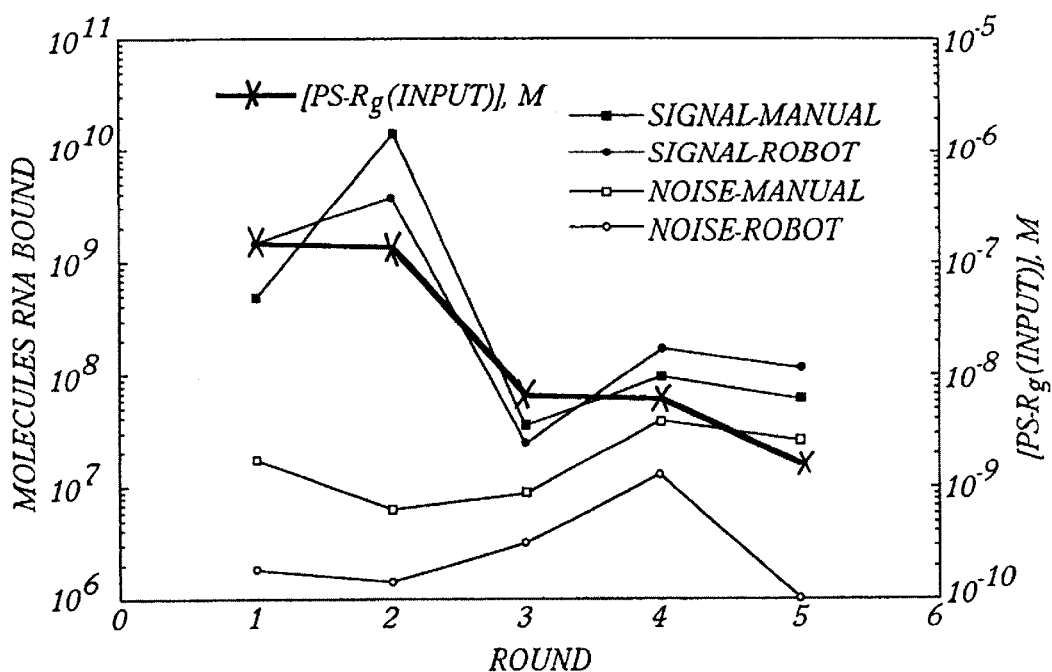

Table 1 below outlines the progress of the PS-Rg SELEX experiment. PS-Rg loading is indicated in µg/ml concentrations. (Binding of PS-Rg to the plate surface has been measured by loading fixed amounts of PS-Rg, washing as described, and then performing a binding curve by titrating high affinity aptamer #1901. This is done with several protein concentrations. The plateau values of these binding curves then are taken as a representation of the amount of active protein bound to the surface, assuming a 1:1 stoichiometry. See FIG. 4. Using these data, it was determined that the plate was near saturated (calculated saturation is 220 fmol/well PS-Rg) when loading 4 µg/ml PS-Rg, representing 150 fmoles of bound PS-Rg). The signal measured represents the number of RNA molecules bound to the wells containing PS-Rg as determined by qPCR for each sample. Similarly, noise is representative of the number of RNA molecules bound to control wells containing no protein. The data in Table 1 is also presented graphically in FIG. 5.

TABLE 1

| Round | PS-Rg, µg/ml Loaded | Signal Manual | Noise Manual | Signal/Noise Manual | Signal Robot | Noise Robot | Signal/Noise Robot |
|---|---|---|---|---|---|---|---|
| 1 | 4 | 4.8e+8 | 1.8e+7 | 2.7 | 1.5e+9 | 1.8e+6 | 833 |
| 2 | 4 | 1.6e+10 | 6.6e+6 | 2424 | 4.2e+9 | 1.5e+6 | 2800 |
| 3 | 0.2 | 4e+7 | 1e+7 | 4 | 2.8e+7 | 3.4e+6 | 8.2 |
| 4 | 0.2 | 1.1e+8 | 4.5e+7 | 2.5 | 2e+8 | 1.5e+7 | 13.3 |
| 5 | 0.2 | 3.1e+8 | 3.1e+7 | 10 | 1.4e+8 | 1e+6 | 140 |

Figure 6:
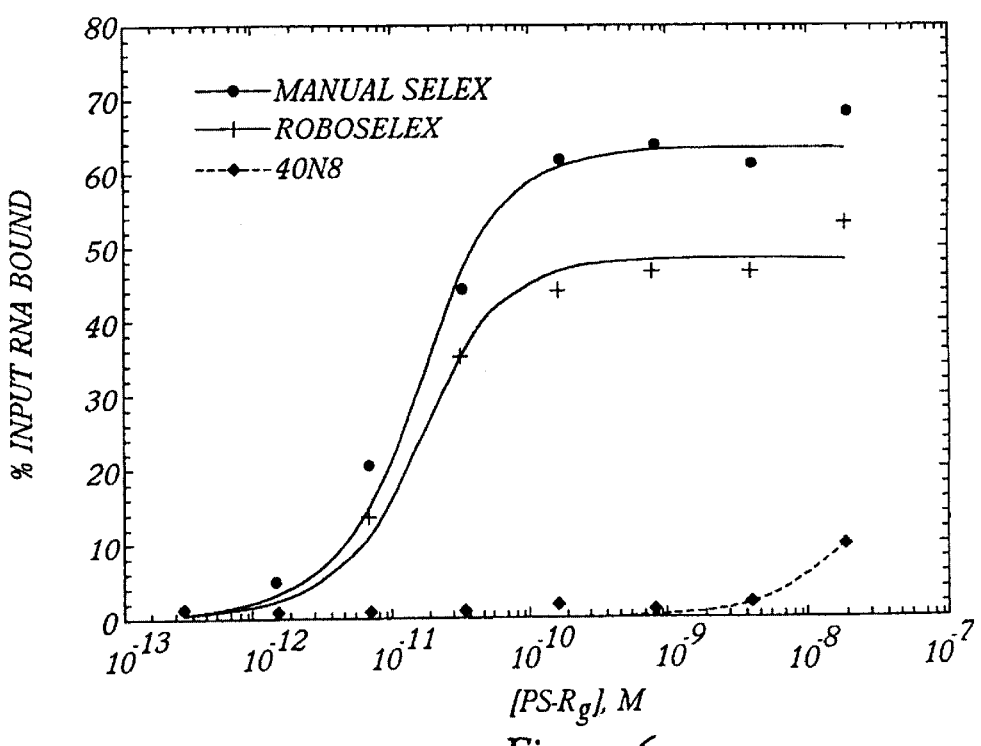
FIG. 6 depicts the solution phase binding curves of round 5 RNA pools to murine PS-Rg protein. The binding curve measured for the enriched round five RNA pool generated with the automated SELEX process (+) is compared to the manual process (filled circles) as well as the starting random RNA pool (filled diamonds).
Figure 7:
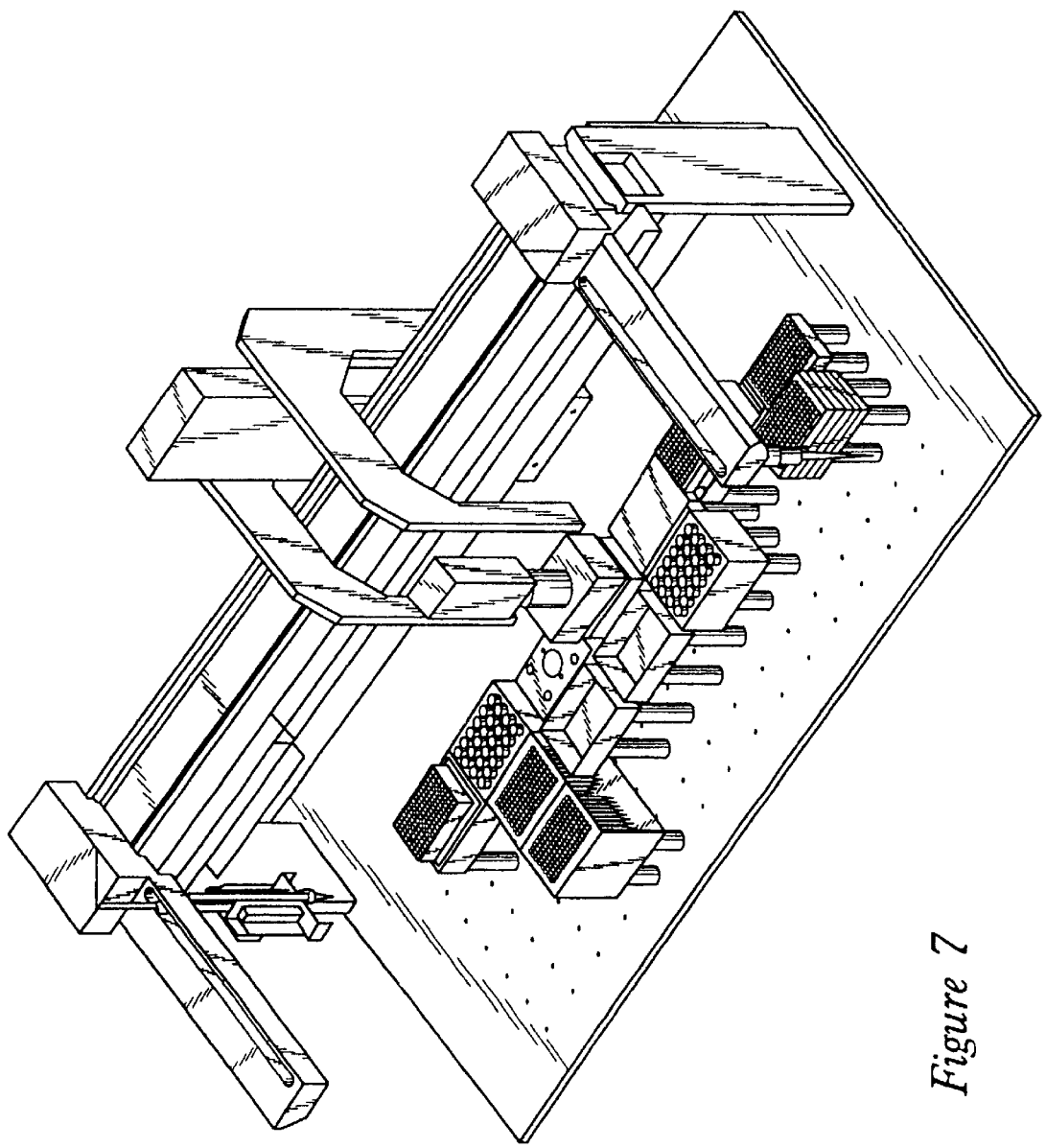
FIG. 7 shows a perspective view of an embodiment of an apparatus for performing automated SELEX according to the present invention.
Figure 8:
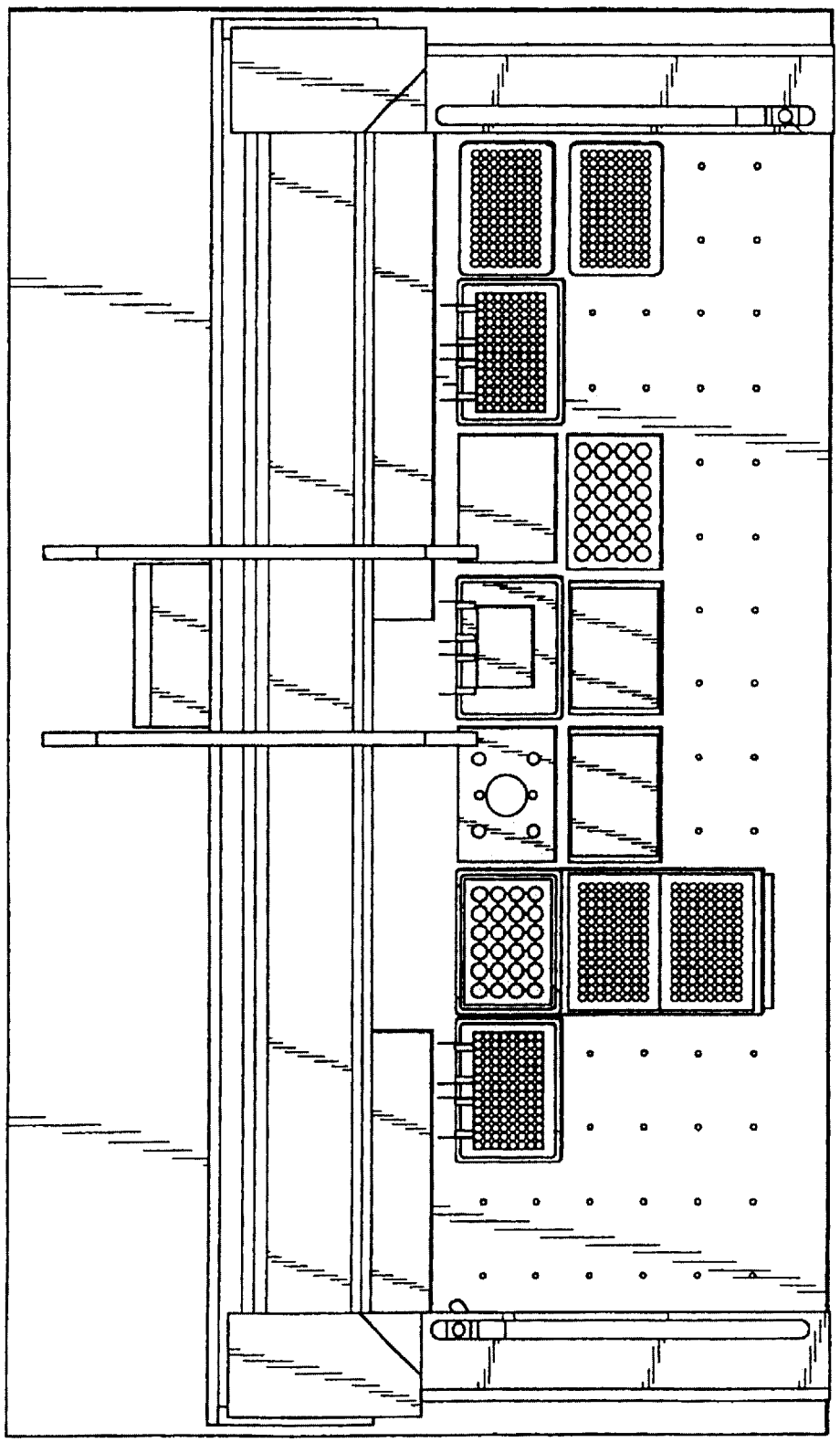
FIG. 8 shows a plan elevation view of an embodiment of an apparatus for performing automated SELEX according to the present invention.
Figure 9:
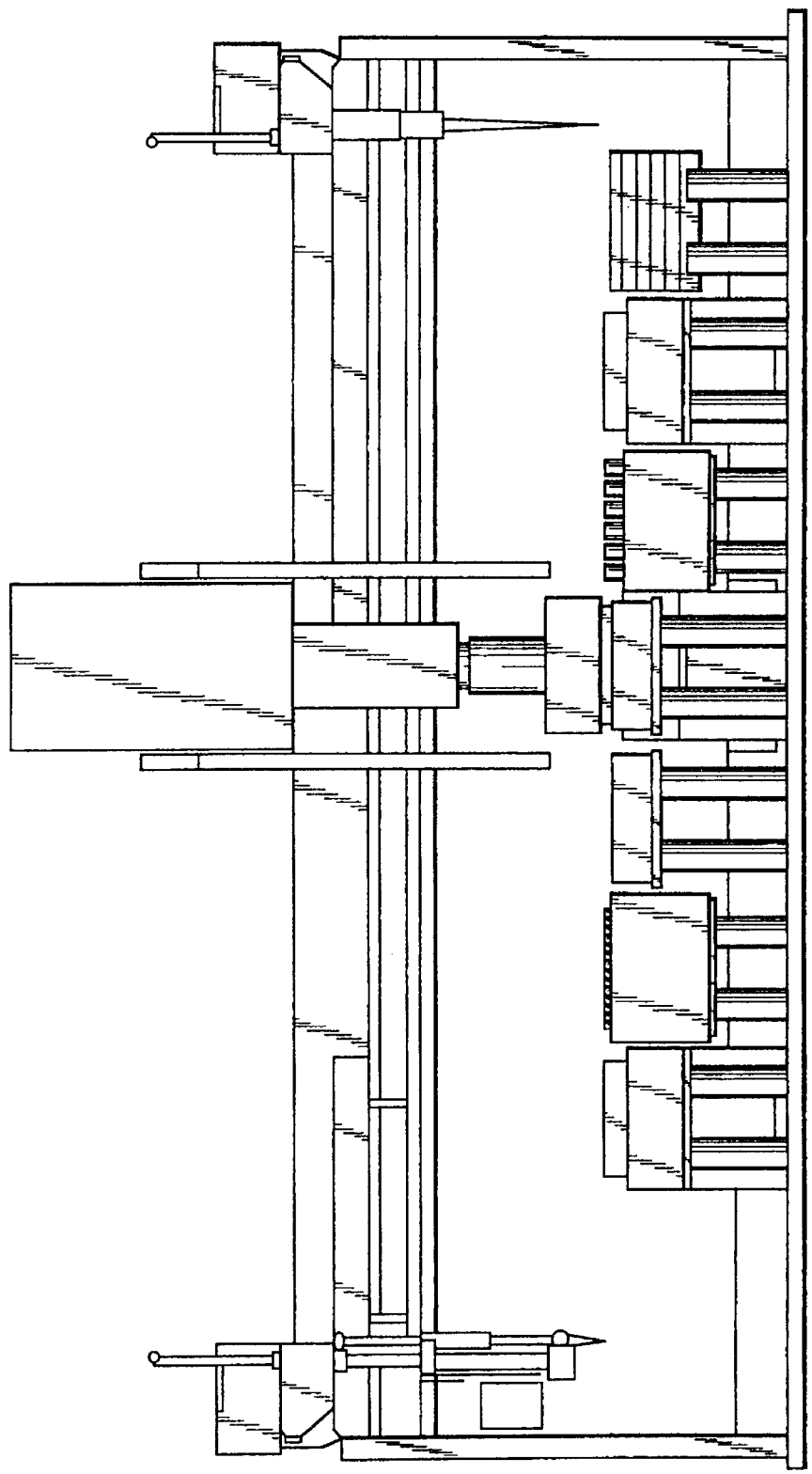
FIG. 9 shows a front elevation view of an embodiment of an apparatus for performing automated SELEX according to the present invention.
Figure 10:
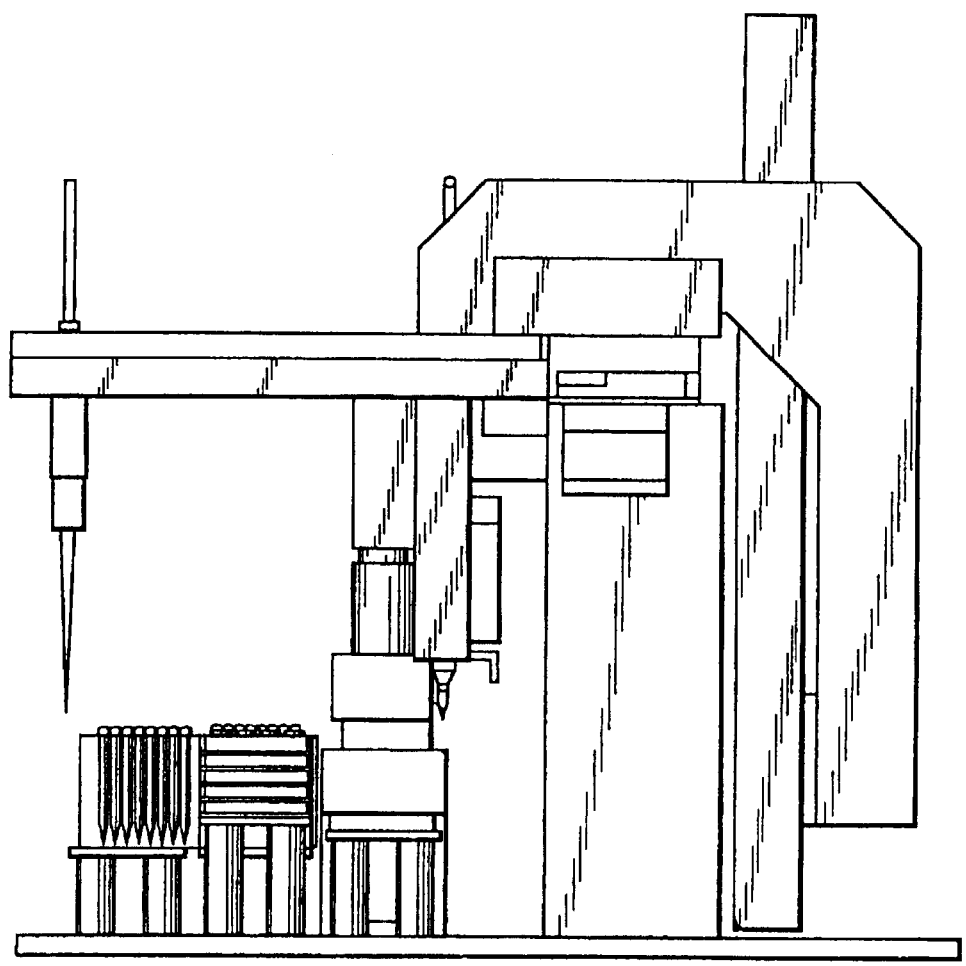
FIG. 10 shows a right side elevation view of an embodiment of an apparatus for performing automated SELEX according to the present invention.

Solution phase binding curves of the enriched round 5 RNA pool from both the automated SELEX process (+) and the manual SELEX process (filled circles), and of the initial RNA candidate mixture (filled diamonds) are illustrated in FIG. 6. It can be seen that relative to the initial candidate mixture, the affinity of the RNA pools from both the manual and the automated SELEX process improved by about 4 orders of magnitude.

Example 3

Quantitative PCR

The following primers (5P7-FD2 and 5P8-FD2) were designed wherein the underlined portions are complementary to the N7 and N8 templates.

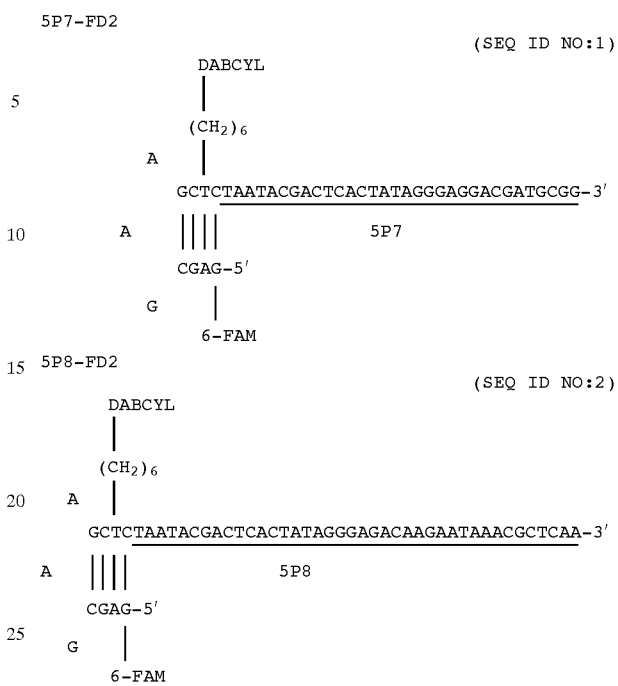

A standard curve using 40N8 cDNA template, primers 5P8 and 3P8 (80 pmoles) and the fluorescent primer 5P8-FD2 (16 pmoles) in a PCR was prepared as a linear plot and and as a semi-log plot (not shown). Template concentrations ranged from $10^6$–$10^{10}$ copies/25 µL reaction. Fluorescein signal (normalized to an internal reference dye and background-subtracted) was plotted as a function of PCR cycle number. In early PCR cycles, product is being generated exponentially in all reactions; however, background signal exceeds product signal. The cycle at which product signal exceeds background is dependent on the starting template copy number. A signal threshold can be chosen above the background level, and the cycle at which each reaction crosses the threshold (Ct) can be plotted as a function of template copy number to generate a standard curve. The equation for the standard curve can then be used to calculate template copy numbers in unknowns based on the Ct values.

This quantitative PCR technique was used to measure signal to noise ratios and absolute template copy number in a SELEX targeting PDGF adsorbed to polystyrene plates. Because very low protein loadings were used (<100 amol/reaction), quantitation by radiation was not possible. An amplification plot (not shown) illustrated quantitation of 10 amol RNA bound to the background well and 600 amol RNA bound to the target well, for a signal-to-noise ratio of 60.

What is claimed is:

1. A method for the automated identification of a nucleic acid ligand from a candidate mixture of nucleic acids, said nucleic acid ligand being a ligand of a given target comprising:
   a) adding the candidate mixture and the target in a predetermined ratio to a reaction vessel at a work station on a work surface using a cartesian robotic manipulator, wherein nucleic acids having an increased affinity to the target relative to the candidate mixture may be partitioned from the remainder of the candidate mixture;
   b) partitioning the increased affinity nucleic acids from the remainder of the candidate mixture using said robotic manipulator;
   c) amplifying the increased affinity nucleic acids to yield an amplified, ligand-enriched mixture of nucleic acids by:
      i) adding primers and polymerase chain reaction reagents to the reaction vessel using said robotic manipulator;
      ii) thermally-cycling the reaction vessel using a thermal cycler while simultaneously measuring the amount of amplified product in said reaction vessel using a measuring device; and
      iii) calculating the amount of increased affinity nucleic acids partitioned at step b) using the measurement of the amount of amplified product obtained from said measuring device;
   d) adjusting the reaction conditions of steps a)–c) in a predetermined manner in response to the amount of nucleic acid ligand calculated at step c) iii); and
   e) repeating steps a)–d) at least once, wherein the adjustments performed at step d) control the stringency of each successive repeat;
wherein said robotic manipulator, said thermocycler, and said measuring device are automatically controlled by a computer during steps a)–e), and wherein said computer automatically calculates the amount of increased affinity product at step c) and automatically adjusts the reaction conditions at step d);
whereby a nucleic acid ligand of said target is identified automatically.

2. The method of claim 1 wherein said target is attached to a solid support, and wherein step (b) is accomplished by automatically partitioning said solid support from said candidate mixture using said robotic manipulator.

3. The method of claim 2 wherein said solid support is a multi-well microtitre plate.

4. The method of claim 3 wherein said plate is comprised of polystyrene.

5. The method of claim 4 wherein said target is attached to said plate by hydrophobic interactions.

6. The method of claim 2 wherein said solid support is a paramagnetic bead and wherein the partitioning of said paramagnetic bead is performed automatically by a magnetic bead separator controlled by said computer.

7. The method of claim 1 wherein said primers are labeled with fluorophores and quenching groups at nucleotide positions that move relative to one another when said primers become incorporated into amplified product, such that the fluorescence emission profiles of said primers change upon incorporation into amplified product, and wherein said measuring device makes the measurement of the amount of amplified product by detecting said change.

8. The method of claim 7 wherein at least one of said primers comprises:
   (a) a single stranded DNA molecule complementary to one of said fixed sequence regions;
   (b) a stem-loop structure attached to the 5' end of said single stranded DNA molecule, said stem comprising a fluorophore and a quenching agent located at nucleotide positions on opposite sides of the stem of said stem-loop structure, said nucleotide positions located sufficiently close to one another such that the fluorescent signal from said fluorophore is substantially quenched by said quenching agent;
wherein the extension of the 3' end of candidate nucleic acid ligands that anneal to said primer during said Polymerase Chain Reaction disrupts said stem structure, wherein said fluorescent group is no longer quenched by said quenching group.

9. The method of claim 8 wherein said primer is selected from the group consisting of:

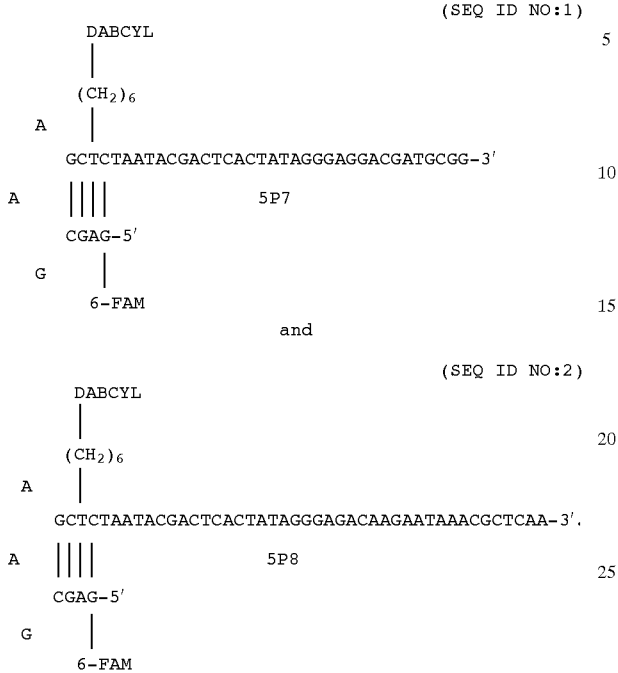

and

10. The method of claim 1, wherein the candidate mixture of nucleic acids is ribonucleic acids, and the method comprises:
   a) adding the candidate mixture and the target in a predetermined ratio to a reaction vessel at a work station on a work surface using a cartesian robotic manipulator, wherein ribonucleic acids having an increased affinity to the target relative to the candidate mixture may be partitioned from the remainder of the candidate mixture;
   b) partitioning the increased affinity ribonucleic acids from the remainder of the candidate mixture using said robotic manipulator;
   c) reverse transcribing the increased affinity ribonucleic acids to produce DNA template by adding reverse transcription reagents to said reaction vessel using said robotic manipulator;
   d) amplifying the DNA template by:
      i) adding primers and polymerase chain reaction reagents to the reaction vessel using said robotic manipulator;
      ii) thermally-cycling said reaction vessel using a thermal cycler while simultaneously measuring the amount of amplified product using a measuring device;
      iii) calculating the amount of increased affinity ribonucleic acids partitioned at step b) using the measurement of the amount of amplified product obtained from the measuring device;
   e) transcribing the amplified DNA to RNA by adding transcription reagents to the reaction vessel using said robotic manipulator;
   f) purifying the transcribed RNA from the amplified DNA by adding RNA specific primers bound to a solid support using said robotic manipulator, whereby only the transcribed RNA binds to the primers;
   g) partitioning the transcribed RNA from the amplified DNA using said robotic manipulator;
   h) adjusting the reaction conditions of steps a)–g) in a predetermined manner in response to the amount of nucleic acid ligand calculated at step d) iii); and
   i) repeating steps a)–h) at least once using the partitioned transcribed RNA of step g) as candidate mixture in step a), wherein the adjustments performed at step h) control the stringency of each successive repeat;

wherein said robotic manipulator, said thermocycler, and said measuring device are automatically controlled by a computer during steps a)–i), and wherein said computer automatically calculates the amount of increased affinity product at step d) and automatically adjusts the reaction conditions at step h);

whereby a ribonucleic acid ligand of said target is automatically identified.

* * * * *